(12) United States Patent
Hu et al.

(10) Patent No.: US 11,644,308 B2
(45) Date of Patent: May 9, 2023

(54) METHOD FOR DETERMINING SLOPE SLIP PLANE WITH GENTLY-INCLINED SOFT INTERLAYER

(71) Applicant: Wuhan University of Science and Technology, Wuhan (CN)

(72) Inventors: Bin Hu, Wuhan (CN); Jing Li, Wuhan (CN); Aneng Cui, Wuhan (CN); Kai Cui, Wuhan (CN); Qinghong Fang, Wuhan (CN); Wei Yang, Wuhan (CN); Yalan Jia, Wuhan (CN); Yang Liu, Wuhan (CN); Xin Zhu, Wuhan (CN)

(73) Assignee: WUHAN UNIVERSITY OF SCIENCE AND TECHNOLOGY, Wuhan (CN)

( * ) Notice: Subject to any disclaimer, the term of this patent is extended or adjusted under 35 U.S.C. 154(b) by 257 days.

(21) Appl. No.: 17/116,278

(22) Filed: Dec. 9, 2020

(65) Prior Publication Data

US 2021/0180948 A1 Jun. 17, 2021

(30) Foreign Application Priority Data

Dec. 12, 2019 (CN) .......................... 201911274321.X

(51) Int. Cl.
*G01B 21/32* (2006.01)
*G01N 33/24* (2006.01)
*E02D 17/20* (2006.01)

(52) U.S. Cl.
CPC ............. *G01B 21/32* (2013.01); *G01N 33/24* (2013.01); *E02D 17/20* (2013.01)

(58) Field of Classification Search
CPC ......... G01B 21/32; G01N 33/24; E02D 17/20
See application file for complete search history.

(56) References Cited

FOREIGN PATENT DOCUMENTS

JP  2007303231 A  * 11/2007

* cited by examiner

Primary Examiner — Jamel E Williams
(74) Attorney, Agent, or Firm — M&B IP Analysts, LLC

(57) ABSTRACT

The disclosure provides a method for determining a slope slip plane with a gently-inclined soft interlayer, including: S1, determining a curve formed with a slip arc of a trailing edge tearing plane, a soft interlayer plane and a slip arc of a leading edge shear opening as a slope slip plane; S2, calculating a slip plane stability coefficient; S3, determination of a position of the gently-inclined soft interlayer plane: if the slip plane stability coefficient is less than 1 but close to 1, determining that the position of the slope slip plane is accurate; otherwise, moving the position of the soft interlayer plane and repeating steps S1 and S2, until the slip plane stability coefficient is less than 1 and close to 1. The method is simple, and has a high accuracy for determining a non-circular slip plane with a soft interlayer as a bottom slip plane.

4 Claims, 3 Drawing Sheets

US 11,644,308 B2

METHOD FOR DETERMINING SLOPE SLIP PLANE WITH GENTLY-INCLINED SOFT INTERLAYER

CROSS REFERENCE TO RELATED APPLICATION

This application claims the priority of Chinese Patent Application No. 201911274321.X, entitled "Method for Determining Slope Slip Plane with Gently-Inclined Soft Interlayer" filed with the Chinese Patent Office on Dec. 12, 2019, which is incorporated herein by reference in its entirety.

TECHNICAL FIELD

The disclosure relates to a method for determining a slope slip plane with a gently-inclined soft interlayer, and belongs to the technical field of slope safety and stability evaluation.

BACKGROUND

Slope stability refers to a stability of slope rock and soil under a certain slope height and slope angle conditions. Unstable natural slopes and artificial slopes with excessively large designed slope angles often slip or collapse under an action of rock and soil gravity, water pressure, vibration force and other external forces. Large-scale slope rock and soil damage can cause traffic interruptions, collapse of buildings, blockage of rivers, and siltation of reservoirs, causing huge losses to people's lives and property.

Slope stability analysis and evaluation is a core of slope engineering. Landslides are a common type of slope instability and failure. an accuracy of the determination of potential slip planes of landslides has a direct impact on landslide treatment. At present, the commonly used methods for determining the slip plane at home and abroad include a limit equilibrium method, a limit analysis method, and a strength reduction method. Wherein the limit equilibrium method and the limit analysis method are mainly applicable to homogeneous slopes whose slip plane is similar to an arc, while not applicable for the determination of a non-circular slip plane with gently-inclined soft interlayers. The strength reduction method determines the slip plane based on a plastic failure zone, but there is a problem that the plastic failure zone is large or the plastic zone cannot be connected.

For non-homogeneous engineering rock slopes with complex geological conditions, the shape of the slip plane is affected by many factors, such as geological structure, geological environment, deformation and failure traces of the slope, etc. Especially for bedding slopes with soft interlayers, slip planes often form along the soft interlayers. This kind of soft interlayer has low mechanical strength and poor hydraulic properties, and under the influence of water, blasting vibration and other factors, the joints and fissures of the slope rock gradually develop, and finally form a connected structural plane, which forms the slope slip plane with the soft interlayer plane. Under the action of gravity, the slope slides along the soft interlayer plane to form a landslide.

During the geological survey, due to unclear geological conditions and ambiguous stratum survey caused by factors such as survey technology and personnel quality, the location of the soft interlayer cannot be accurately determined. For slopes where the location of the soft interlayer cannot be determined and a certain amount of slip deformation has occurred, the accuracy of the determination of the slip plane is related to the design and construction of subsequent landslide treatment. Unreasonable landslide treatment design caused by the uncertain position of the slip plane is easy to form a safety hazard, endangering the lives of construction personnel and the safety of equipment.

SUMMARY

In order to solve the deficiencies in the prior art, the disclosure provides a method for determining the slope slip plane with the gently-inclined soft interlayer. The method is simple and has a high accuracy for determining a non-circular slip plane with a soft interlayer as a bottom slip plane, which provides a basis for a design of landslide treatment schemes for slopes with gently-inclined soft interlayers.

In order to achieve the above objective, the technical solution of the disclosure provides a method for determining the slope slip plane with the gently-inclined soft interlayer, comprising following steps of:

S1. determination of the slope slip plane:

S1.1. determination of a slip arc of a trailing edge tearing plane: in a case of assuming that a soft interlayer plane is at a certain depth, selecting a starting point A and an ending point B of a slip deformation produced at the trailing edge of the slip plane, drawing an arc tangent to the soft interlayer plane through the two points A and B to get a tangent point C, and taking an arc ABC as the slip arc of the trailing edge tearing plane;

S1.2. determination of a slip arc of the leading edge shear opening: selecting a leading edge shear point D of the slip plane, and in a case of assuming that the leading edge of the slip plane is sheared horizontally, drawing an arc tangent to both a horizontal line and the soft interlayer plane through the point D according to a tangent length theorem, to get a tangent point E between the arc and the soft interlayer plane; and taking an arc ED as the slip arc of the leading edge shear opening;

wherein a curve formed with the slip arc of the trailing edge tearing plane, the soft interlayer plane and the slip arc of the leading edge shear opening is taken as the slope slip plane;

S2. calculating a slip plane stability coefficient with a limit equilibrium method; and S3. determination of a position of the gently-inclined soft interlayer plane: if the slip plane stability coefficient calculated in step S2 is less than 1 but close to 1, determining that the position of the slope slip plane is accurate; otherwise, moving the position of the soft interlayer plane and repeating steps S1 and S2, until the slip plane stability coefficient is less than 1 and close to 1.

Further improvements to the technical solution of the disclosure includes:

the limit equilibrium method in step S2 is a Morgenstern-Price method or an imbalance thrust force method suitable for a non-circular slip;

a stratum of the trailing edge of the slip plane in step S1.1 is a quaternary soil layer; and a stratum of the leading edge of the slip plane in step S1.2 is gravelly soil.

It can be seen from the technical scheme provided by the disclosure that, according to the method for determining the slope slip plane with the gently-inclined soft interlayer of the disclosure, in a case of first assuming that the soft interlayer plane is at a certain depth, the starting point A and the end point B of the slip deformation produced at the trailing edge of the slip plane are selected to determine the position of the slip arc of the trailing edge tearing plane; in a case of assuming that the leading edge of the slip plane is sheared horizontally, the position of the slip arc of the leading edge shear opening is obtained according to the tangent length theorem; wherein the slip arc of the trailing edge tearing plane, the soft interlayer plane and the slip arc of the leading edge shear opening form the slope slip plane; the slip plane stability coefficient is calculated with the limit equilibrium method to determine whether the position of the slope slip plane is accurate based on the stability coefficient. This method is very simple, wherein, the slip arc of the trailing edge tearing plane can be determined only by drawing an arc tangent to the soft interlayer plane through the point A and the point B, and the slip arc of the leading edge shear opening can be determined only by drawing an arc tangent to both a horizontal line and the soft interlayer plane through the point D. The position accuracy of the slope slip plane can be determined by repeatedly calculating the slip plane stability coefficient. And the closer the stability coefficient is to 1, the higher the determined position accuracy of the slip plane is. The accurate slip plane position can provide an important basis for the formulation of the subsequent slope landslide treatment scheme, thereby preventing irrational landslide treatment design caused by an inaccurate position of the slip plane, and ensuring the safety of construction personnel and equipment.

In the figures: 1. slip arc of trailing edge tearing plane; 2. soft interlayer plane; 3. produced slip rock; 4. slip arc of leading edge shear opening; 5. slope slip plane; 6. quaternary soil; 7. gravelly soil; 8. limestone.

DETAILED DESCRIPTION OF THE EMBODIMENTS

The disclosure will be further described below with reference to the drawings and embodiments.

Figure 1:
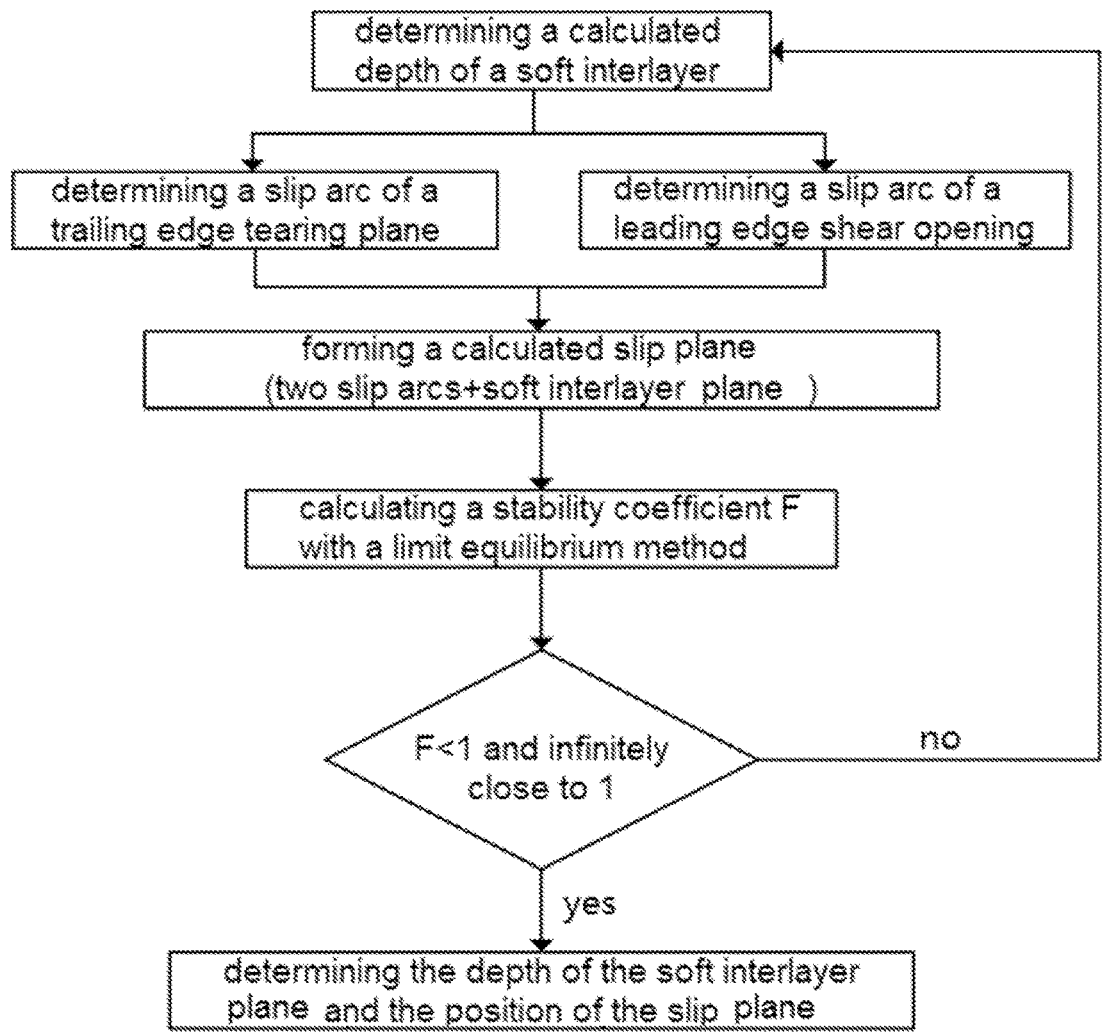
FIG. 1 is an overall flow chart of the disclosure.
Figure 2:
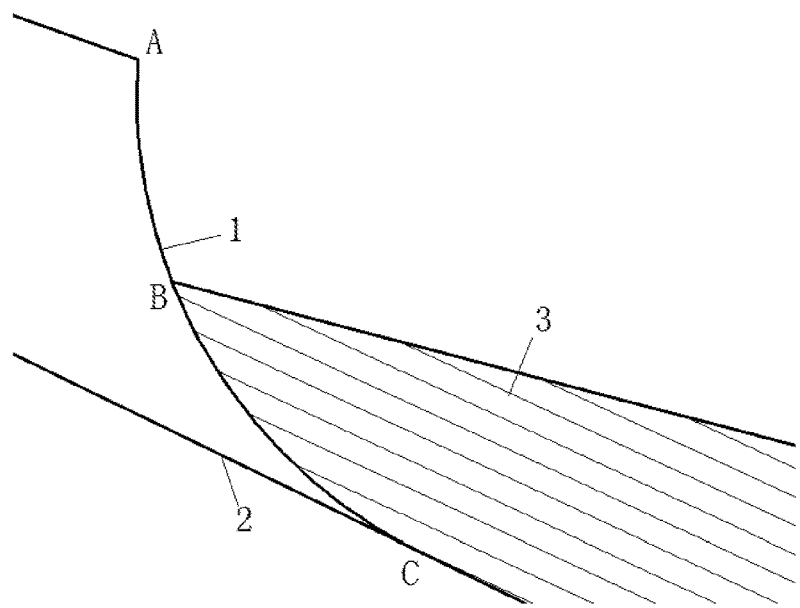
FIG. 2 is a schematic diagram of determining a slip arc of a trailing edge tearing plane.
Figure 3:
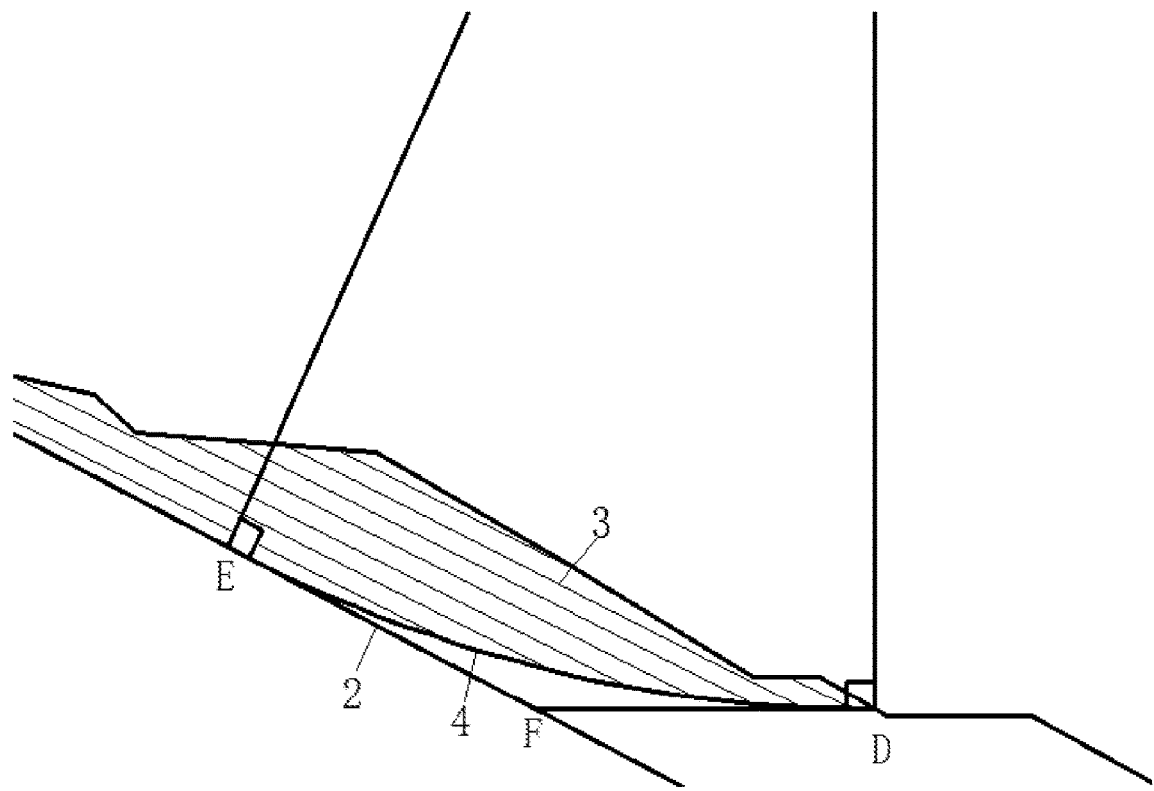
FIG. 3 is a schematic diagram of determining a slip arc of a leading edge shear opening.
Figure 4:
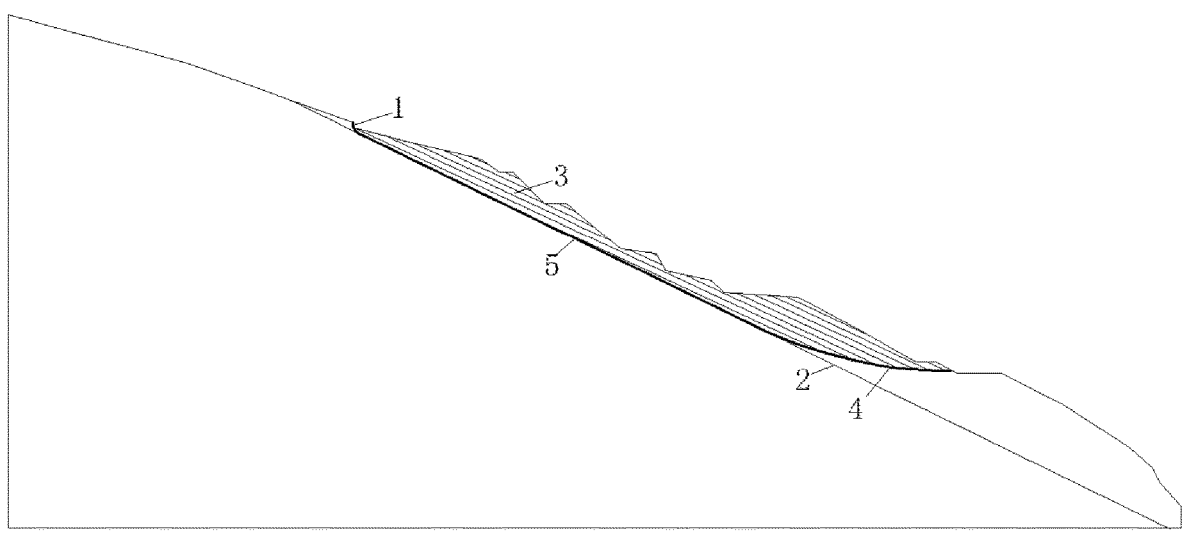
FIG. 4 is a schematic diagram of a slip plane determined by an embodiment of the disclosure.

As shown in FIG. 1, the method for determining the slope slip plane with the gently-inclined soft interlayer provided by this embodiment includes steps S1-S3:

S1. determination of the slope slip plane:

S1.1. determination of a slip arc of a trailing edge tearing plane 1: in a case of assuming that the soft interlayer plane 2 is an inclined plane at a certain depth, a starting point A and an ending point B of a slip deformation produced at the trailing edge of the slip plane of the produced slip rock 3 are selected, as shown in FIG. 2; an arc tangent to the soft interlayer plane through the two points A and B is drawn to get a tangent point C, and the arc ABC is taken as the slip arc of the trailing edge tearing plane 1;

S1.2. determination of the slip arc of the leading edge shear opening 4: as shown in FIG. 3, a leading edge shear point D of a slip plane of the produced slip rock 3 is selected; assuming that the leading edge of the slip plane is sheared horizontally, an intersection point between the horizontally sheared line and the soft interlayer plane is F; and an arc tangent to both the horizontal line and the soft interlayer plane 2 through the point D is drawn according to the tangent length theorem to get a tangent point E between the arc and the soft interlayer plane, and the arc ED is taken as the slip arc of the leading edge shear opening 4;

as shown in FIG. 4, a curve formed with the slip arc of the trailing edge tearing plane 1, the soft interlayer plane 2 and the slip arc of the leading edge shear opening 4 is taken as the slope slip plane 5;

S2. calculation of the slip plane stability coefficient with the limit equilibrium method: the slip plane stability coefficient is calculated by using the Morgenstern-Price method or the imbalance thrust force method suitable for a non-circular slip;

wherein, the imbalance thrust force method is:

$$F = \frac{\sum_{i=1}^{n-1}\left(R_i \prod_{j=i+1}^{n} \psi_j\right) + R_n}{\sum_{i=1}^{n-1}\left(T_i \prod_{j=i+1}^{n} \psi_j\right) + T_n};$$

the Morgenstern-Price method is:

$$M_n(F, \lambda) = \int_a^b \left(X - E\frac{dy}{dx}\right)dx - \int_a^b \frac{dQ}{dx} h_e dx = 0.$$

S3. determination of a position of the gently-inclined soft interlayer plane: if the slip plane stability coefficient F calculated in step S2 is less than 1 but close to 1, the position of the slope slip plane is determined to be accurate; otherwise, the position of the soft interlayer plane is moved and steps S1 and S2 are repeated, until the slip plane stability coefficient F is less than 1 and close to 1.

Figure 5:
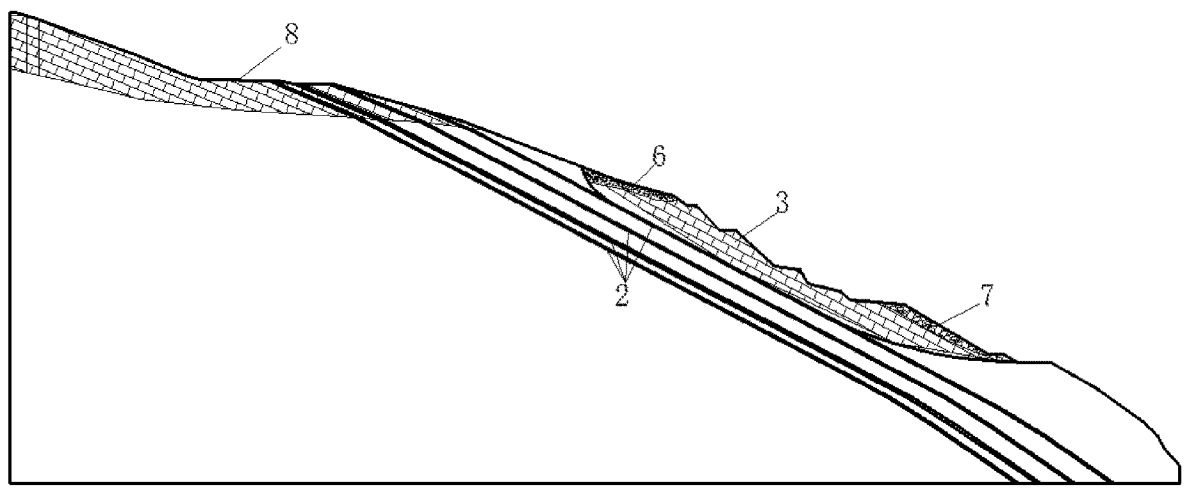
FIG. 5 is a slope geological model diagram according to an embodiment of the disclosure.

The slope model with gently-inclined soft interlayer in this embodiment is shown in FIG. 5, which includes limestone 8, a soft interlayer 2, gravel soil 7, and quaternary soil 6. An accuracy of the position of the slip plane is simulated with a rainfall conditions and a stability coefficient of 1.0. Wherein, the slope rock parameters of the gently-inclined soft interlayer arc shown in Table 1, and the slip plane stability coefficients at different depths of the soft interlayer calculated by the limit equilibrium method are shown in Table 2. The calculation shows that the depths of the slip plane of the soft interlayer are between 23-26 m, and a more specific depth of the slip plane of the soft interlayer can be determined by further calculations. In this embodiment, Slide limit equilibrium analysis software is used to perform calculations. Computer-aided calculation makes the calculation process more convenient, faster, and more accurate.

TABLE 1

| slope rock parameters of the gently-inclined soft interlayer | | | | | | |
|---|---|---|---|---|---|---|
| lithology | c(MPa) | φ(°) | E(GPa) | $\sigma_t$(MPa) | μ | ρ(g/cm³) |
| soft interlayer | 0.010 | 22.00 | 0.67 | 0.008 | 0.3 | 2.020 |
| limestone | 1.030 | 31.01 | 1.5 | 1.200 | 0.24 | 2.680 |
| $Q_4$ | 0.015 | 16.00 | 0.04 | 0 | 0.37 | 2.004 |

Wherein, c is cohesion, φ is internal friction angle, E is elastic modulus, $\sigma_t$ is tensile strength, μ is Poisson's ratio, and ρ is density.

TABLE 2

| slip plane stability coefficients at different depths of the soft interlayer | |
|---|---|
| depth/m | stability coefficient (rainfall condition) |
| 17 | 0.964 |
| 20 | 0.971 |
| 23 | 0.984 |
| 26 | 1.001 |
| 29 | 1.014 |

The above-mentioned specific embodiments are merely explanations of the disclosure, not a limitation of the disclosure. Any modification, equivalent replacement, improvement, etc. made within the spirit and principle of the disclosure shall fall into the protection scope of the disclosure.

In the method for determining the slope slip plane with the gently-inclined soft interlayer of the disclosure, the most important step is to determine a depth position of the soft interlayer. Herein, the slip plane stability coefficient is calculated through the limit equilibrium method, the stability coefficient is used to determine whether the position of the soft interlayer is accurate, and after the position of the soft interlayer is determined, the slope slip plane with the gently-inclined soft interlayer is formed with the position of the soft interlayer, the slip arc of the trailing edge tearing plane and the slip arc of the leading edge shear opening. This method is simple and reliable, and can determine the position of the slip plane under the condition of satisfying a certain accuracy, which provides a basis for the design of the landslide treatment scheme for the slope with the gently-inclined soft interlayer.

The invention claimed is:

1. A method for determining a slope slip plane with a gently-inclined soft interlayer, comprising following steps of:
   S1. determination of the slope slip plane by a computer:
   S1.1. determination of a slip arc of a trailing edge tearing plane: in a case of assuming that a soft interlayer plane is at a certain depth, selecting a starting point A and an ending point B of a slip deformation produced at the trailing edge of the slip plane, drawing an arc tangent to the soft interlayer plane through the two points A and B to get a tangent point C, and taking an arc ABC as the slip arc of the trailing edge tearing plane;
   S1.2. determination of a slip arc of a leading edge shear opening: selecting a leading edge shear point D of the slip plane, and in a case of assuming that the leading edge of the slip plane is sheared horizontally, drawing an arc tangent to both a horizontal line and the soft interlayer plane through the point D according to a tangent length theorem, to get a tangent point E between the arc and the soft interlayer plane; and taking an arc ED as the slip arc of the leading edge shear opening;
   wherein a curve formed with the slip arc of the trailing edge tearing plane, the soft interlayer plane and the slip arc of the leading edge shear opening is taken as the slope slip plane;
   S2. calculating a slip plane stability coefficient with a limit equilibrium method by the computer;
   S3. determination of a position of the gently-inclined soft interlayer plane by the computer: if the slip plane stability coefficient calculated in step S2 is less than 1 but close to 1, determining that the position of the slope slip plane is accurate; otherwise, moving the position of the soft interlayer plane and repeating steps S1 and S2, until the slip plane stability coefficient is less than 1 and close to 1; and
   S4. designing a landslide treatment scheme for a slope with the gently-inclined soft interlayer based on the position of the gently-inclined soft interlayer plane.

2. The method for determining the slope slip plane with the gently-inclined soft interlayer according to claim 1, wherein the limit equilibrium method in step S2 is a Morgenstern-Price method or an imbalance thrust force method suitable for a non-circular slip.

3. The method for determining the slope slip plane with the gently-inclined soft interlayer according to claim 1, wherein a stratum of the trailing edge of the slip plane in step S1.1 is a quaternary soil layer.

4. The method for determining the slope slip plane with the gently-inclined soft interlayer according to claim 1, wherein a stratum of the leading edge of the slip plane in step S1.2 is gravelly soil.

* * * * *